United States Patent [19]

Grumet et al.

[11] Patent Number: 4,471,056
[45] Date of Patent: Sep. 11, 1984

[54] METHOD FOR HLA-DR TYPING OF TOTAL HUMAN LYMPHOCYTE SAMPLE

[75] Inventors: Frank C. Grumet, Stanford; Edgar G. Engleman, Atherton, both of Calif.

[73] Assignee: The Board of Trustees of the Leland Stanford Junior University, Stanford, Calif.

[21] Appl. No.: 364,997

[22] Filed: Apr. 2, 1982

[51] Int. Cl.³ .................... G01N 33/50; G01N 33/54; G01N 33/80
[52] U.S. Cl. .................... 436/513; 424/11; 436/519; 436/548; 436/821
[58] Field of Search .................. 424/11; 436/513, 519, 436/63, 548

[56] References Cited

U.S. PATENT DOCUMENTS

| | | | |
|---|---|---|---|
| 4,124,701 | 11/1978 | Bach | 436/519 |
| 4,239,746 | 12/1980 | Bartos | 424/11 |
| 4,328,183 | 5/1982 | Rosenfield | 424/11 |
| 4,403,042 | 9/1983 | Henry | 436/519 |
| 4,420,558 | 12/1983 | De Mey | 436/519 X |

FOREIGN PATENT DOCUMENTS 17381 10/1980 European Pat. Off. .
18795 11/1980 European Pat. Off. .

OTHER PUBLICATIONS

J. Van Wauwe et al., Immunology, 42 (1), 157–164 (Jan. 1981).
van Rood, J. J. et al., Nature, 262, 795–797 (1976).
Report of the Eighth International Histocompatibility Workshop; Articles by A. van Leeuwen et al., pp. 278–279; by C. Bland et al., pp. 280–282; by A. Longo et al., pp. 283–284; by A. H. Johnson et al., pp. 285–286; and by J. A. Danilovs et al., pp. 287–288.

Primary Examiner—Sidney Marantz
Attorney, Agent, or Firm—Ciotti & Murashige

[57] ABSTRACT

An HLA-DR typing test based on lymphocytotoxicity in which a vital dye-labeled total human lymphocyte sample, such as a sample of peripheral blood lymphocytes, is incubated with HLA-DR antisera, a monoclonal antibody against T cells, and complement and the DR type is determined based upon the resultant cytotoxicity as measured by the fluorescence of B cells surviving the incubation.

10 Claims, No Drawings

METHOD FOR HLA-DR TYPING OF TOTAL HUMAN LYMPHOCYTE SAMPLE

DESCRIPTION

1. Technical Field

The invention is in the field of immunology. More particularly it relates to an improved HLA-DR typing test.

2. Background Art

The major histocompatability complex (MHC) of humans is a cluster of genes occupying a region located on the sixth chromosome. This complex, denoted HLA (Human Leukocyte Antigen), is currently divided into five major gene loci, which according to World Health Organization nomenclature are designated HLA-A, HLA-B, HLA-C, HLA-D, and HLA-DR. The products of the HLA genes are commonly called "antigens". The genes of the A, B, and C loci encode the classical transplantation antigens whereas the genes of the D and DR loci most probably encode antigens that control immune responsiveness. HLA antigens are present in the membranes of human cells. Some are present in most cells of the body whereas others are present only in specific kinds of cells. For instance, HLA-DR antigens have been identified in B cells but not in resting T cells.

The HLA antigens are categorized into types that vary from individual to individual. HLA typing is used in paternity determinations, transplant and transfusion compatability testing, blood component therapy, anthropological studies, and in disease association correlation to diagnose diseases or to predict susceptibility to disease. Current HLA-DR typing techniques consist of two basic methods (Joint Report from 8th International Histocompatibility Testing Workshop, 1980, Los Angeles). One involves separating B cells from a total lymphocyte sample, e.g. peripheral blood lymphocytes (PBL), treating the B cells with anti-DR sera and complement, and reading the resultant cytotoxicity as an index of reactivity. The B cells are separated from the total lymphocyte population because DR antigens are present only in B cells and B cells constitute only a small proportion, typically 10% to 25%, of PBL. Cytotoxicity of such a small proportion of cells would be difficult to discern accurately. Numerous methods have been used previously to separate B cells from PBL. The most common method takes advantage of the reaction of T cells with sheep erythrocytes (SRBC) to form rosettes that can be centrifuged through a layer of Ficoll-Hypaque, leaving the B cells at the top of the gradient. Other methods take advantage of the affinity of B cells for various materials such as nylon wool, Degalon beads, and anti-human F(ab')$_2$ reagent. These methods suffer from various combinations of being time consuming or technically difficult, yielding impure preparations (i.e. contamination with non-B lymphocytes), providing poor absolute yields of testable B cells or, yielding separated B cells that have poor viability.

Monoclonal antibodies against HLA-DR antigens have been used to separate B cells from PBL for use in HLA-DR typing tests (de Krester, et al, *Tissue Antigens* (1980) 16:317–325).

The second basic HLA-DR typing method is the two color fluorescence technique (Van Rood, J. J., et al, *Nature* (1976) 262:795). In this method, to label B cells with an immunofluorescent marker, a PBL preparation is incubated with a fluorochrome labeled anti-human Ig, washed, and then dispensed in tissue typing trays. Following sequential incubations with DR antisera and complement the test results are read by determining the percent of viable B cells remaining by adding a fluorescent vital dye and measuring percent viability only of those cells having ring immunofluorescence. Although this method avoids a B cell separation step, it requires that the cells be stained with anti-human Ig. It also is practical only when read under high power microscopy and, therefore, has a more demanding reading step than the B cell separation method.

Monoclonal antibodies that bind specifically to T cells are known (Royston, et al, *J Immunol* (1980) 125:725; European patent application No. 80300829.1 (publication number 0 017 381); and European patent application No. 80301357.2 (publication No. 0 018 795).

A principal object of the present invention is to provide a simple and effective HLA-DR typing technique that (1) does not involve a B cell separation step or a lymphocyte staining step and (2) is based on cytotoxicity function such that the sera and complement used in available lymphocytotoxicity tests may be used in the invention method.

DISCLOSURE OF THE INVENTION

One aspect of the invention is a B cell antigen typing method comprising:

(a) incubating a total human lymphocyte sample with
 (i) an antibody against the B cell antigen that activates complement;
 (ii) an anti-human T cell antibody that activates complement;
 (iii) complement; and (b) determining whether the B cell antigen is present in the B cells in the sample by the resultant cytotoxicity.

Another aspect of the invention is a test kit for carrying out the above described method comprising in association:

(a) an antibody against the B cell antigen that activates complement;
(b) an anti-human T cell antibody that activates complement; and
(c) complement.

MODES FOR CARRYING OUT THE INVENTION

The invention method may be used to type any antigen that is present on B cells but not T cells. Antigens that are present exclusively on B cells are referred to herein as "B cell antigens". While the most prevalent use of the method will be to type HLA-DR antigens, it may be used to determine the type of other B cell antigens such as B cell differentiation antigens. For convenience, the following description of the modes for carrying out the invention concerns the embodiment that is used to type HLA-DR antigens.

The typing method of the invention is based on lymphocytotoxicity. Although various human tissues may be used to obtain a total lymphocyte sample (i.e. a population of T cells and B cells that has not been fractionated to separate B cells) for the typing test, peripheral blood is the most convenient source. At least about five ml of peripheral blood is needed for the test. Lymphocytes may be separated from the blood by density gradient centrifugation. This involves layering the blood over a gradient medium of appropriate specific gravity.

The most suitable gradient media for separating lymphocytes from red cells and granulocytes are high molecular weight polymers such as Ficoll (a cross-linked epichlorohydrin-sucrose polymer), Ficoll-Hypaque, and Lymphoprep. The layered blood is centrifuged using a low centrifugal field that avoids disrupting the cell membranes, usually 300 ×g for 20 to 30 min. The lymphocytes layer on top of the gradient medium and the red cells and granulocytes pass through. Platelets are removed either by defibrinating the blood before density gradient centrifugation or by differential centrifugation. Preferably the blood is defibrinated beforehand and the cells are suspended in a balanced salt solution at a cell:solution volume ratio of 1:1 for centrifuging. Following gradient centrifugation the lymphocytes are harvested from the interface and washed with balanced salt solution to remove residual gradient medium. The lymphocytes may then be suspended in a growth medium, usually at $3 \times 10^6$ to $6 \times 10^6$ cells/ml, pending use. The cells may be stored more or less indefinitely by freezing in liquid nitrogen.

The total lymphocyte sample is incubated with three reagents: (1) anti-DR sera; (2) anti-T cell antibody; and (3) complement. The anti-DR sera may be obtained from human hosts that have been immunized with HLA-DR antigen. Anti-HLA-DR antibodies are induced in human hosts by pregnancy, blood transfusion, or tissue grafting. The most useful source of HLA-DR typing sera is women immunized by pregnancy, since they will have been exposed to a limited number of foreign HLA-DR antigens. HLA-DR antisera are available in predispensed typing trays from various sources such as the National Institute of Allergy and Infectious Diseases. The typing method will preferably be carried out using a panel of such sera that are each substantially monospecific for a particular DR antigen type.

The anti-T cell antibody reagent used in the typing is one that binds to all T cells, i.e. both regulatory and effector T cells, rather than to a particular subpopulation of T cells. It must not bind to B cells and must activate complement rapidly and extensively. Such antibodies are commonly called pan T cell antibodies. Antibodies of the IgM class and most subclasses of IgG antibodies activate complement when they bind to antigens. The anti-T cell antibody is preferably of the IgM class because IgMs are strong complement activators. The reagent may be composed of an antibody that binds specifically to T cells in general or a mixture of antibodies that individually bind to particular T cell subpopulations but combined bind to the entire T cell population.

The anti-T cell antibody reagent is preferably a monoclonal antibody of the IgM class that binds to T cells but not to other lymphocytes. Such monoclonal antibodies may be produced via the somatic cell hybridization technique (Kohler and Milstein, *Nature* (1975) 256:495–7) using an immunization protocol biased toward generating cytotoxic IgM antibodies. The antibody-producing fusion partner is prepared by immunizing a host, preferably mice, with human PBL. The PBL may be isolated from whole blood as described above. About $40 \times 10^6$ cells are used for the immunization. Preferably lymphoid cells are obtained from the inguinal and axillary lymph nodes of the host during the primary immune response and presumably before significant suppressor cell activity or somatic cell mutations of $V_H$ genes can occur. Harvest will usually be done about 3 days post-immunization. This early harvest maximizes the likelihood of obtaining IgM-producing lymphoid cells. The lymphoid cells are hybridized (fused) with an appropriate myeloma cell line using a fusogen such as polyethylene glycol having a Mw of about 1000 to 6000 daltons. A myeloma cell line that is sensitive to a selective medium such as HAT medium (Littlefield, *Science* (1969) 145:709–710), that fuses efficiently, and that will support stable, high level expression and secretion of antibody by its hybridization partner is used. While myeloma cells from any species may be used, murine myeloma lines having these characteristics are available currently and are preferred. Examples of such lines are those derived from the original MOPC-21 and MPC-11 mouse tumors that are available from the Salk Institute Cell Distribution Center, PO Box 1809, San Diego, Calif. 92112. Lymphoid:myeloma cell ratios of about 0.2:1 to about 10:1 may be used, with a ratio of about 5:1 being preferred. The individual cell concentrations will typically be in the range of $10^6$ to $10^8$, preferably $1 \times 10^7$ to $5 \times 10^7$ cells/ml fusion medium. Balanced salt solutions containing 30% to 60% (w/v), preferably about 50% (w/v) fusogen, may be used as a fusion medium.

After the fusion the cells are washed with fusogen-free medium to remove fusogen. They are then seeded and cultivated in the selective medium (HAT) to eliminate unhybridized parent cells and leave only hybrids that are resistant to the selective medium and possess the immortality of the myeloma parent. The cultivation will normally take at least about 10 to 14 days. Surviving hybridomas may be examined for production of anti-T cell antibody by a standard microlymphocytotoxicity assay using T cell and B cell targets (Lizak, G. E., Grumet, F. C., *Human Immunology* (1980) 1:87). Positive hybridomas may be cloned by limiting dilution techniques and grown in vitro or in vivo by known procedures. Monoclonal antibody produced by the hybridoma clones may be harvested from the culture medium or ascites fluid by known procedures such as ammonium sulfate precipitation, DEAE cellulose chromatography, or affinity chromatography. Further purification of the antibody, if desired, may be achieved by ultracentrifugation and microfiltration.

Rabbit serum is typically used as the complement reagent in HLA typing tests based on lymphocytotoxicity. It is believed to contain sublytic antihuman antibody which helps produce cell death. It is available commercially from Buxted, Pel-Freez, and others. Complement from other animal sources may be used provided that it produces the desired degree of cytolysis.

The incubation of the PBL with the DR antisera, anti-T cell antibody preparation, and complement is carried out under conditions that permit binding between the antibodies and complement activity and will support cells not affected by the incubation. Multi-well typing trays are available for containing the incubation mixture. A conventional cell growth medium containing serum will normally be used as an incubation medium. The pH of the medium is physiological (pH 7.2 to 7.4). The antibody reagents will typically be used in equivolume amounts relative to the PBL, whereas the complement is normally used in a substantial volume excess, e.g. at least about 5:1 to 10:1, relative to the PBL sample. A preferred protocol is to first incubate the DR antisera with the PBL and allow the antisera to bind with any HLA-DR antigens present in the B cells in the PBL sample. The anti-T cell antibody is then added and the mixture is incubated to allow it to bind to the T cells in the PBL. The temperature at which the antisera and anti-T cell antibody incubations are carried out is preferably about 37° C. The complement is then added and the mixture in incubated, preferably at about 22° C., to allow the complement to be fixed by the antigen-antibody complexes. Such fixation will result in cytolysis of all the T cells in the test mixture and those B cells with which the DR antisera have reacted. In instances where a DR antiserum does not react with the B cell antigens of the sample there will be a readily detectable number of residual viable B cells.

Cytolysis may be detected and measured by loss of a vital dye, e.g. intracellular fluorescein or carboxyfluorescein, retained by living cells, or leakage of $^{51}$Cr or other labels from injured cells. Comparison of the test samples with negative controls permits an accurate determination of whether the PBL sample contains a particular HLA-DR antigen. A preferred cytotoxicity determination procedure uses the vital dye carboxyfluorescein diacetate as a label that is administered to the PBL before the incubation. This dye is taken up, activated, and concentrated by living cells. Cytolysis permits the dye to diffuse from the lysed cells, thereby causing lysed cells to lack fluorescence. Fluorescence in this preferred cytotoxicity determination procedure may be read with a standard fluorescent microscope. The live cells that survive the incubation fluoresce green. The dead cells are indistinguishable in the dark background. Readings may be made visually or by automated technology that detects and quantifies residual intracellular fluorescence.

The following examples further describe the invention. These examples are not intended to limit the invention in any manner. The materials and methods used were as follows.

Preparation of PBL Samples

Peripheral blood was drawn from healthy volunteers into acid citrate dextrose (ACD) tubes and divided into aliquots. Some aliquots were held for three days at room temperature before being processed further while others were processed within 24 hr after collection. Peripheral blood lymphocytes were isolated from the aliquots by density gradient centrifugation of defibrinated peripheral blood samples using Ficoll-Hypaque gradient medium at room temperature, $300 \times g$. The PBL was placed in Beckman tubes and cryopreserved in liquid nitrogen pending use. The freezing medium consisted of 3% bovine serum albumin in Hank's balanced salt solution, 20% glucose in RPMI 1640, and 10% dimethyl sulfoxide.

B Cell Separation for Comparison Tests

Separation of B cells from fresh PBLs prepared as above was performed either by SRBC rosetting (Gmelig-Meyling, F., Ballieux, R. E., *Vox Sang* (1977) 33:5-8) or on Degalon bead columns (Milford, E. L., et al, *Human Immunology* (1980) 1:274). Enriched B cell populations were resuspended in 95% fetal calf serum and 5% dimethyl sulfoxide for cryopreservation in liquid nitrogen.

DR Antisera

Oiled Terasaki trays preloaded with DR antisera defining the antigens DR1 through DRw10 at one $\mu$l/well were used.

Anti-T Cell Monoclonal Antibody

For immunization, $4 \times 10^7$ PBL obtained from a blood donor (HLA type A2, A28; B27, Bw44; Cw4, Cw2) were suspended in phosphate buffered saline (PBS) and administered into each footpad of a 6-week old BALB/c female mouse. Three days post-immunization the inguinal and axillary lymph nodes and the spleen were harvested, and the lymphoid cells were suspended in Dulbecco's Modified Eagle's Medium (DMEM). For fusion the lymphoid cells were mixed at a ratio of 5:1 with SP2/08A2 mouse myeloma cells, centrifuged at $400 \times g$ for 10 minutes at 22° C., and the pellet resuspended in 1 ml of 50% polyethylene glycol (mw1500) in DMEM. This mixture was gradually resuspended into 7 ml DMEM over a six-minute period at room temperature, centrifuged, and ultimately resuspended in DMEM supplemented with 15% newborn calf serum (NCS) in a final concentration of 10 million viable cells per cc. One-tenth cc of this cell suspension was then placed into each of 60 wells of a 96 well tissue culture plate. Following overnight incubation at 37° C. in 6% $CO_2$, each well received an equal volume of 15% NCS in DMEM supplemented with $8.0 \times 10^{-5}$M hypoxanthine, $2 \times 10^{-7}$M aminopterin and $1.3 \times 10^{-5}$M thymidine (HAT) for selection of fused cells. On each of the following three days, half of the volume of each well was replaced with fresh HAT medium. By day 10 those wells showing continued growth in the HAT medium had supernatant samples drawn off to test for antibody activity by a standard microlymphocytotoxicity assay using T cell and B cell targets. One parent well contained a clone, subsequently named TM1, which exhibited specificity for T cells but not B cells or monocytes. It is believed that TM1 antibody binds to the red blood cell rosette receptor. This clone was selected and subcloned in vitro by the method of limiting dilution. Syngeneic mice, pretreated with Pristane intraperitoneally (ip), were given approximately 10 to $30 \times 10^6$ of the cloned TM1 cells ip and the resultant ascites fluid was harvestd over the next several weeks for use directly in the invention DR typing method.

Complement

Eight week old rabbit serum (Pel-Freez, Rogers, Arizona) locally prescreened for cytotoxic activity against B and T lymphocytes was used.

Invention Typing Method

Frozen PBL samples were thawed rapidly in a 37° C. water bath. When only a small crystal of ice remained the Beckman tube was filled slowly with 20% heat-inactivated fetal calf serum (HIFCS) in RPMI. The cell suspension was transferred to a 1.5 cc tube and the tube was filled with 20% HIFCS/RPMI and centrifuged for 3 min at room temperature, $300 \times g$. The supernatant was removed and discarded. A working solution of carboxyfluorescein diacetate (c-FDA) was made by diluting a stock acetone solution of c-FDA (10 mg/ml) in phosphate buffered saline (PBS) at 1:250. The cell pellet was resuspended gently in 150 $\mu$l of the c-FDA working solution and the suspension was incubated at 37° C. for 15 min in the dark. Following the incubation one ml of 20% HIFCS/RPMI was added and the suspension was tranferred to a $12 \times 75$ mm tube.

The cell suspension was then underlayered with one ml of 10% Ficoll-Hypaque and centrifuged at $350 \times g$ for 6 min at 20° C. The cell interface was removed and diluted to approximately 1.4 ml with 20% HIFCS/RPMI, and the suspension was centrifuged for 3 min at room temperature, 300×g. The supernatant was removed and the cell pellet was resuspended in 20% HIFCS/RPMI to approximately 5000 cells/μl (about 100 μl of 20% HIFCS/RPMI).

The viability of cells was checked by adding one drop of 0.4% ethidium bromide to one drop of the cell suspension. Live cells fluoresce green and dead cells fluoresce orange under a fluorescent microscope.

One μl of the c-FDA labeled cell suspension was added to each test well of the preloaded Terasaki tray and the tray was incubated for ½ hour at 37° C. in the dark. One μl of the anti-T cell monoclonal antibody preparation diluted 1:20 in 3% bovine serum albumin in Hank's basic salt solution was then added to the wells. Two negative control sera were used on the tray. Monoclonal antibody was not added to one of them to provide a control for the activity of the monoclonal antibody. The tray was then uncubated for ½ hr at 37° C. in the dark. Ten μl of the pretested rabbit complement reagent was then added to each well and the tray was incubated for 2 hr at 20° C. in the dark. The tray was then blotted with an absorbant paper to remove oil in the wells and facilitate readings.

A small volume from the top of each well was removed and read under a 6X objective on a standard fluorescent microscope using either dark field or epiillumination with appropriate excitation and barrier filters for fluorescein fluorescence. Dead cells are not visible since they have lost their intracellular fluorescence. Live cells will fluoresce green. The cell death (i.e., fluorescence) of the test wells are compared to that of the negative control well to determine the DR type of the sample PBL. Cytotoxicity is scored on a scale of 1 to 8, using the negative control well as a relative "100%" assigned viability standard; thus 8 = 85%–100% relative cell death
6 = 50%–85% relative cell death
4 = <50% relative cell death.

Comparison Typing of B Cell Enriched Populations

Enriched B cell populations were treated with c-FDA as described above and diluted with 20% HIFCS/RPMI into a concentration of 2×10 per cc. One μl of the cell suspension was added to each well of DR alloantisera loaded Terasaki trays and the trays were incubated at 37° C. for one hour. Five μl of complement were then added to each well and following a second incubation at 20° C. the trays were read in the manner described above.

HLA-DR typing of nine individuals was carried out using the invention method and the comparison typing methods. Details and results of these tests are reported in the table below.

| DR Sera | | DR TYPING Results | | | | | | | | |
|---------|---|---|---|---|---|---|---|---|---|---|
| Specificity and Name | Other DR Specificities | CG (DR5,w10) 1 S 2 3 | DN (DR5,7) 1 S 2 3 | LF (DR4,—) 1 2 | BF (DR7,—) 1 3 | BI (DR1,4) 1 3 | JB (DR2,w6) 1 2 | AM (DR2,3) 1 3 | MK (DRw6,w8) 1 3 | TK (DRw9,—) 1 3 |
| DR1: B4289 | | | | | | 8 8 | | | | |
| Bode | | | | | | 6 8 | | | | |
| Lewan | | | | | | 8 8 | | | | |
| DR2: JoneC | DRw6 | | | | | | 6 4 | 8 6 | 6 | |
| Olsen | | | | | | | 6 4 | 8 6 | | |
| Rinde | | | | | | | 6 4 | 6 4 | | |
| S3066 | | | | | | | 6 6 | 6 8 | | |
| S8332 | | | | | | 6 | 6 4 | 8 6 | | |
| DR3: Berge | | | | | | | | 8 4 | | |
| Lake | | | | | | | | 8 4 | | |
| Lilli | | | | | 6 | | | 6 4 | | |
| Pett | Drw6 | | | | 4 6 | | | 8 6 | | |
| Tate | | | | | | | | 6 | | |
| DR4: Bra77 | | | | | 6 6 | 6 6 | | | | |
| Murph | | | | | 8 6 | 6 6 | | | | |
| Niels | | | | 6 | 4 | 6 6 | | | | |
| DR5: N1107 | DRw6 | 6 N | 6 6 6 6 | | | | | | 6 | |
| Ocken | DRw6 | 6 8 6 4 | 8 8 8 6 | 4 | 4 | | 4 | | 6 | |
| Stiev | | 8 8 6 4 | 8 8 6 N | 6 | | | | 4 | 4 | N |
| SKI74 | | 6 8 6 4 | 8 8 6 6 | | | | | | | |
| Cu30 | DRw8 | 6 6 6 | 8 8 8 6 | 6 | 6 | | | 4 4 | 6 | |
| JB153 | | 6 N | 6 6 8 N | | | | | | | |
| Drw6: JoneC | DR2 | | | | | | 6 4 | 8 6 | 6 | |
| JoneL | DR3 | | | | | | 6 4 | 8 8 | 6 | |
| Ocken | DR5 | 6 8 6 4 | 8 8 8 6 | 4 | 4 | | 4 | | 6 | |
| Carne | DR1,DR2 | | | | 6 | 4 6 | 6 4 | 8 6 | 6 4 | |
| Charl | | | | | | | 4 | | 6 | 6 4 |
| DR7: Chadw | | | 8 8 6 8 | | 6 | | | | | |
| L701 | DR3 | | 8 8 6 6 | | 6 | | | | | |
| JH371 | | | 6 8 8 8 | | 6 4 | | | | | |
| Me712 | | | 8 8 6 6 | | 6 | | | | | |
| Schul | DR2 | | 8 8 6 | | 6 | | | | | |
| DRw8: Kubic | | | | | | | | | 8 6 | |
| DRw9: Culps | DRw10 | 6 8 6 6 | | | | | | | | 8 4 |
| JR50 | | 6 | | | | | | | | 8 6 |
| DRw10: Chan | | N N 6 4 | | | | | | | | |
| Culps | DRw9 | 6 8 6 6 | | | | | | | | 8 |

-continued

| DR Sera | | DR TYPING Results | | | | | | | | |
|---|---|---|---|---|---|---|---|---|---|---|
| Specificity and Name | Other DR Specificities | CG (DR5,w10) 1 S 2 3 | DN (DR5,7) 1 S 2 3 | LF (DR4,—) 1 2 | BF (DR7,—) 1 3 | BI (DR1,4) 1 3 | JB (DR2,w6) 1 2 | AM (DR2,3) 1 3 | MK (DRw6,w8) 1 3 | TK (DRw9,—) 1 3 |
| NW145 | | 6 8 6 | | | | | | | | |

Method:
1 = TM1 treated PBLs
S = TM1 treated PBLs stored at room temperature for 3 days before isolation and cryopreservation
2 = B cell enriched - Degalon beads
3 = B cell enriched - SRBC-rosetting
Cytotoxicity scored on a standard scale of 1 to 8. For simplicity all spaces with negative (ie "1") reactions are left blank.
N = Not done.

In all cases the DR typing reactions in the TM1 technique were at least as strong and clear as the comparison method(s). It is also noteworthy that even for samples that had been stored for 3 days (before PBL isolation) TM1 typings were clear and strong. Similar 3 day storage experiments were not tried with the comparison DR typing methods because extensive prior experience had shown such storage to be extremely deleterious to typing by those methods. In addition to the serological data shown in the table, additional cells covering all of the alloantigens DR1-DRw10 were typed by the TM1 method and either or both of the comparison methods, and in every case the phenotype assignments by the TM1 method results were at least as good and generally better, than the comparison method.

Comparisons of post-cryopreservation yields of cells suitable for DR typing, per $10^6$ PBLs isolated from starting whole blood, showed the following ranges: (1) SRBC-rosetting, $0.5-1.0\times10^5$, with 80%-95% B cell purity (defined by reactivity with the monomorphic, monoclonal anti-DR antibody L243); (2) Degalon beads, $0.3-0.6\times10^5$, with 90%-100% purity; (3) TM1, $0.5-1.0\times10^5$, with 90%-100% purity. It should also be noted that qualitatively the reactivity was judged by the technologists performing the typing to be in the order TM1 $\geq$ Degalon > SRBC-rosetting.

The test kits for carrying out the invention DR typing method will contain as basic ingredients given amounts of each DR antiserum, the anti T-cell antibody, and complement. These ingredients will be dispensed in suitable containers. The kit will also typically include a cytotoxicity marker, e.g. a vital dye, gradient medium, and directions for performing the method. The DR antisera may optionally be preloaded into typing trays or an unloaded typing tray may be included in the kit. The kit components may be packaged in a conventional manner.

Modifications of the above described modes for carrying out the invention that are obvious to those of ordinary skill in the immunodiagnostic art or related arts are intended to be within the scope of the following claims.

We claim:
1. An HLA-DR typing method comprising:
   (a) incubating a total human lymphocyte sample with
      (i) an anti-HLA-DR antibody that activates complement;
      (ii) and anti-human T cell antibody that activates complement; and
      (iii) complement; and
   (b) determining whether the HLA-DR antigen to which the anti-HLA-DR antibody binds is present in the B cells in the sample by comparing the viable B cell content of the incubated sample with a negative control.

2. The method of claim 1 wherein the sample is a sample of peripheral blood lymphocytes.

3. The method of claim 1 or 2 wherein the anti-human T cell antibody is a monoclonal antibody.

4. The method of claim 3 wherein the monoclonal antibody is of the IgM class.

5. The method of claim 1 or 2 wherein the complement is rabbit complement.

6. The method of claim 1 or 2 wherein the sample is labeled with a vital dye before the incubation and the resultant cytotoxicity is based on the loss of the vital dye by lysed cells.

7. The method of claim 6 wherein the vital dye is carboxyfluorescein diacetate.

8. The method of claim 2 wherein the anti-human T cell antibody is a monoclonal antibody of the IgM class; the complement is rabbit complement; the sample is labeled with carboxyfluorescein diacetate before the incubation and the resultant cytotoxicity is based on the loss of the label by lysed cells.

9. The method of claim 1, 2, or 8 wherein the incubation of the sample with the HLA-DR antibody, anti-human T cell antibody, and complement is carried out in separate steps.

10. The method of claim 9 wherein the HLA-DR antibody incubation step and the anti-human T cell antibody incubation step are each carried out at about 37° C. and the complement incubation step is carried out at about 22° C.

* * * * *